(12) United States Patent
Greene et al.

(10) Patent No.: US 8,567,338 B2
(45) Date of Patent: Oct. 29, 2013

(54) REPROCESSING INDICATOR FOR SINGLE PATIENT USE MEDICAL INSTRUMENTS

(75) Inventors: Jack Greene, Mason, OH (US); Paul T. Marshall, Cincinnati, OH (US); Mark H. Ransick, West Chester, OH (US); Mark S. Leuenberger, Loveland, OH (US); Danny R. Kelley, Cincinnati, OH (US); George M. Pomeroy, Cincinnati, OH (US); Gregory Frey, Indianapolis, IN (US); William B. Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 178 days.

(21) Appl. No.: 12/111,728

(22) Filed: Apr. 29, 2008

(65) Prior Publication Data
US 2009/0266289 A1    Oct. 29, 2009

(51) Int. Cl.
*G01D 21/00*    (2006.01)

(52) U.S. Cl.
USPC ........... 116/206; 116/200; 283/100; 428/42.1

(58) Field of Classification Search
USPC ......... 116/200, 210, 206, 207, 216, 278, 280, 116/DIG. 1, DIG. 14, DIG. 41; 422/55–58, 422/119; 436/1, 3; 283/100–101, 901; 235/380, 383, 385, 487–489, 375, 494; 428/138, 913, 916, 42.1
See application file for complete search history.

(56) References Cited

U.S. PATENT DOCUMENTS

| | | | | |
|---|---|---|---|---|
| 2,578,150 A * | 12/1951 | Rathke | ......................... | 426/132 |
| 2,654,170 A * | 10/1953 | Nestor | ......................... | 40/310 |
| 3,311,084 A * | 3/1967 | Edenbaum | ................... | 116/207 |
| 3,592,682 A * | 7/1971 | Weiner et al. | .................. | 28/350 |
| 3,702,511 A * | 11/1972 | Miller | ......................... | 40/306 |
| 3,835,564 A * | 9/1974 | Gottschalk | ................... | 40/306 |
| 3,891,242 A * | 6/1975 | Arnold et al. | ................ | 283/101 |
| 4,049,121 A * | 9/1977 | White | ........................ | 206/439 |
| 4,082,873 A * | 4/1978 | Williams | .................... | 428/42.1 |
| 4,444,839 A * | 4/1984 | Dudzik et al. | ................. | 428/336 |
| 4,479,838 A * | 10/1984 | Dunsirn et al. | ............... | 156/247 |
| 4,614,367 A * | 9/1986 | Breen | ........................ | 283/102 |
| 4,718,553 A * | 1/1988 | Adamoli et al. | ........... | 206/459.1 |
| 4,837,061 A * | 6/1989 | Smits et al. | .................. | 428/41.1 |
| 4,846,504 A * | 7/1989 | MacGregor et al. | .......... | 283/102 |
| 4,994,314 A * | 2/1991 | Rosenfeld et al. | ......... | 428/36.92 |
| 5,042,842 A * | 8/1991 | Green et al. | ................. | 283/101 |
| 5,060,848 A * | 10/1991 | Ewan | .......................... | 229/102 |
| 5,329,713 A * | 7/1994 | Lundell | ......................... | 40/310 |
| 5,411,295 A * | 5/1995 | Bates et al. | ..................... | 283/81 |
| 5,451,372 A * | 9/1995 | Larsson et al. | ................ | 422/424 |
| 5,569,163 A * | 10/1996 | Francis et al. | ................ | 600/133 |
| 5,622,764 A * | 4/1997 | Battles | ............................ | 428/52 |
| 5,633,058 A * | 5/1997 | Hoffer et al. | ................. | 428/40.1 |
| 5,660,925 A * | 8/1997 | Cooley et al. | ............. | 428/304.4 |
| 5,779,686 A | 7/1998 | Sato et al. | | |

(Continued)

FOREIGN PATENT DOCUMENTS

WO    WO2004/114256    12/2004

*Primary Examiner* — Peter Macchiarolo
*Assistant Examiner* — Tania Courson
(74) *Attorney, Agent, or Firm* — Welsh Flaxman & Gitler LLC

(57) ABSTRACT

A medical instrument including an indicator of exposure to fluids applied to the medical instrument.

13 Claims, 14 Drawing Sheets

(56) References Cited

U.S. PATENT DOCUMENTS

| | | | |
|---|---|---|---|
| 5,895,075 A * | 4/1999 | Edwards | 283/81 |
| 6,220,633 B1 * | 4/2001 | Van Boom et al. | 283/100 |
| 6,238,623 B1 * | 5/2001 | Amhof et al. | 422/426 |
| 6,447,014 B1 * | 9/2002 | Seidl | 283/81 |
| 6,455,119 B2 * | 9/2002 | Carides et al. | 428/42.2 |
| 6,575,919 B1 * | 6/2003 | Reiley et al. | 600/567 |
| 6,659,036 B2 * | 12/2003 | Omatsu et al. | 116/206 |
| 6,828,018 B2 * | 12/2004 | Waterbury et al. | 428/354 |
| 7,105,225 B2 * | 9/2006 | Birkholz et al. | 428/354 |
| 7,185,601 B2 * | 3/2007 | Carpenter et al. | 116/206 |
| 7,287,691 B2 * | 10/2007 | Montanari | 235/380 |
| 7,732,046 B2 * | 6/2010 | LaBrosse et al. | 428/343 |
| 7,744,997 B2 * | 6/2010 | Birkholz et al. | 428/354 |
| 7,892,639 B2 * | 2/2011 | Mess et al. | 428/354 |
| 8,037,545 B2 * | 10/2011 | McLaughlin | 2/69 |
| 8,360,323 B2 * | 1/2013 | Widzinski et al. | 235/488 |
| 8,440,274 B2 * | 5/2013 | Wang | 428/34.1 |
| 2002/0066219 A1 * | 6/2002 | Weidman et al. | 40/913 |
| 2003/0211618 A1 * | 11/2003 | Patel | 436/38 |
| 2004/0210167 A1 | 10/2004 | Webster | |
| 2005/0036719 A1 * | 2/2005 | Wu et al. | 383/105 |
| 2005/0113808 A1 * | 5/2005 | Berndt | 606/1 |
| 2006/0025814 A1 * | 2/2006 | Hatori | 606/205 |
| 2006/0054526 A1 * | 3/2006 | Dean et al. | 206/459.1 |
| 2006/0069305 A1 * | 3/2006 | Couvillon et al. | 600/117 |
| 2006/0236913 A1 * | 10/2006 | Wills | 116/206 |
| 2007/0130811 A1 * | 6/2007 | Shevelev et al. | 40/312 |
| 2007/0215001 A1 * | 9/2007 | Voegele | 106/31.01 |
| 2007/0219563 A1 * | 9/2007 | Voegele | 606/108 |

* cited by examiner

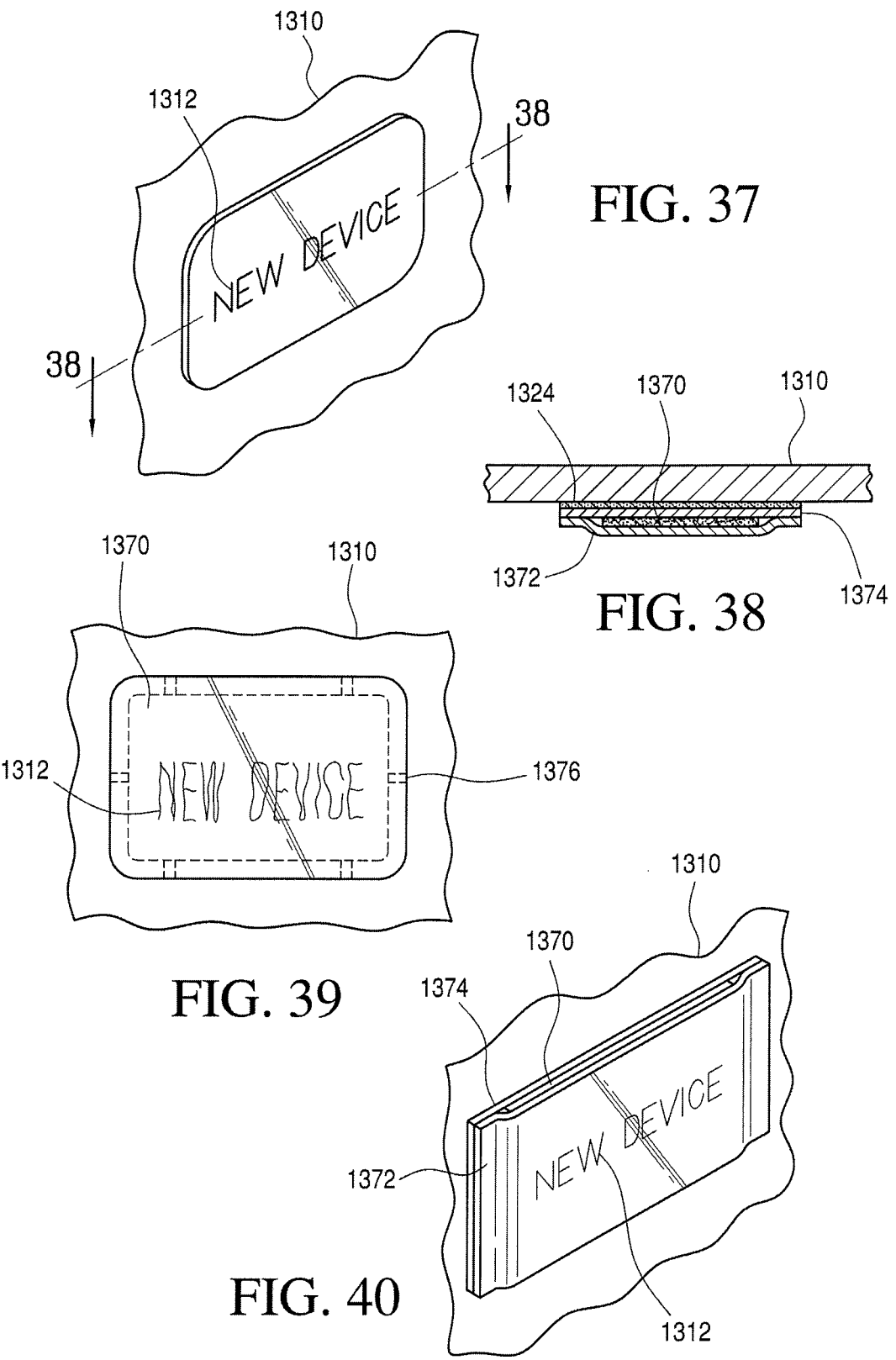

REPROCESSING INDICATOR FOR SINGLE PATIENT USE MEDICAL INSTRUMENTS

BACKGROUND OF THE INVENTION

1. Field of the Invention

The invention relates to various indicators for identifying reprocessed medical instruments. More particularly, the invention relates to the utilization of various inks for the identification of reprocessed medical instruments.

2. Description of the Related Art

Engineers specializing in the design and manufacture of medical instruments commonly attempt to improve upon previously existing medical instruments by enhancing the usage of these instruments. By improving the medical instrument, the possibility for user error is often drastically reduced. Through improved engineering, these engineers attempt to eliminate the gap between the best surgeon and the worst surgeon through careful product design. Similarly, they try to transform patient care through inventive product design. Many of their medical instruments are designed for minimally invasive procedures, resulting in quicker surgeries, lower risk of complications, less pain, shorter recovery time and lower costs.

The development of improved manufacturing techniques, advanced materials and concerns regarding contamination have led to the development of medical instruments designed for single use applications. For example, many laparoscopic devices, such as, surgical staplers and trocars, are designed as single use items that are intended to be immediately disposed of after use.

A recent trend in the medical community is reprocessing of single use medical instruments, by parties other than the original equipment manufacturer, instead of discarding them after use. During reprocessing, the medical instruments are disassembled, cleaned and sterilized. They are then reassembled for future use.

However, many of the medical instruments reprocessed for further use are specifically designed only for use during a single procedure. Consequently, the performance of the medical instruments decline after reprocessing, since the components making up the medical instrument are not adapted for multiple uses and will degrade in performance when used beyond their intended life span. For example, reprocessing of the cutting devices on trocars extends these devices beyond their intended mission life and may result in duller blades. A greater force, therefore, is needed to make an initial incision, causing more trauma to the patient. In addition, the use of greater force increases the potential for error during the surgical procedure.

The reprocessing itself can also cause serious problems. Some of the components of single use medical instruments cannot be reused. Thus, the reprocessor must manufacture these components. The third party reprocessors often do not satisfy the tolerances required for proper operation of the medical instruments as the third party reprocessors do not have the in-depth knowledge of the device application or design required to create proper replacement parts.

As reprocessing of medical instruments proliferates, it has become very difficult to identify if an item has in fact been reprocessed or if it is the original medical instrument delivered by the original manufacturer. Doctors usually do not even know if a medical instrument has been reprocessed, since the medical instrument is commonly unpacked prior to use by the doctor and any reprocessing notification is located on the packaging of the medical instrument. The FDA requires labeling of the reprocessed item with the new manufacturer information; however the medical instrument itself is not required to be marked permanently and a removable tag is allowed. In fact, some hospitals instruct the staff responsible for opening medical instruments and setting up the medical instruments for surgery not to inform the doctor as to whether the medical instruments have been reprocessed.

Often, when these medical instruments have been reprocessed and used for a second, third or fourth time, they fail and are returned to the original product manufacturer, for example, assignee Ethicon Endo Surgery, Inc., of the present invention. The original manufacturers are commonly obligated to replace defective products (i.e., those original medical instruments which are defective and have not been reprocessed) and have them returned for analysis. However, there is no economical way to distinguish between a product that failed as a result of some defect in the original manufacture thereof and one that failed because of third party reprocessing.

SUMMARY OF THE INVENTION

It is, therefore, an object of the present invention to provide a medical instrument. The medical instrument includes a medical instrument body and a label including an indicator of exposure to fluids or solvents applied to the medical instrument body.

It is also an object of the present invention to provide a medical instrument wherein the indicator is a water soluble ink incorporated into material composition of the label.

It is another object of the present invention to provide a medical instrument wherein the indicator is a film printed with inks providing an indication of reuse or reprocessing of the medical instrument.

It is a further object of the present invention to provide a medical instrument wherein the film is a clear film and includes a first surface that is exposed for viewing when the label is applied to the medical instrument body and a second surface that faces the medical instrument body, and ink is printed upon the second surface which is not visible until contact with a fluid.

It is also an object of the present invention to provide a medical instrument wherein a mechanism is provided in the label for exposing the ink on the second surface to fluid when the medical instrument is in contact with a fluid.

It is another object of the present invention to provide a medical instrument wherein the label is opaque and includes a first surface which is exposed for viewing upon application to the medical instrument body and a second surface which faces the medical instrument body and hidden from view, and adhesive bonds the second surface to medical instrument in a manner permitting release of the label upon exposure to fluid revealing markings applied to the surface of the medical instrument.

It is a further object of the present invention to provide a medical instrument wherein the indicator is an indicator symbol composed of reactive ink such that the reactive ink turns color when exposed to various processing environments.

It is also an object of the present invention to provide a medical instrument wherein the indicator symbol includes section marked with reactive ink, and each section is printed with a unique reactive ink.

It is another object of the present invention to provide a medical instrument wherein a color scale is provided near each indicator ink that shows a user an expected color when the reactive ink does turn color.

It is a further object of the present invention to provide a medical instrument wherein the label is positioned on or around a seam of the medical instrument body.

It is also an object of the present invention to provide a medical instrument wherein the seam includes an underlying graphics image which is revealed upon removal of the label.

It is another object of the present invention to provide a medical instrument wherein the indicator includes a top printing layer and an opaque background printed using soluble inks. A message is printed beneath the top printing layer and the background, the message being composed of permanent inks, such that when reprocessed, the top printing layer and the background are removed exposing the message.

It is a further object of the present invention to provide a medical instrument wherein the label includes trace amounts of uniquely detectable chemicals or compounds such that when present they can be detected by analytical equipment.

It is also an object of the present invention to provide a medical instrument wherein the label includes a top layer and a base layer, and the top layer delaminates from the base layer upon exposure fluid.

It is another object of the present invention to provide a medical instrument wherein the base layer includes a message.

It is a further object of the present invention to provide a medical instrument wherein the top layer and base layer are optically interactive.

It is also an object of the present invention to provide a medical instrument wherein the indicator is a permanent ink which changes color after a period of time to indicate time of exposure.

It is another object of the present invention to provide a medical instrument wherein the indicator is an absorptive material sensitive to specific substances.

It is a further object of the present invention to provide a medical instrument a medical instrument body, a medical instrument component connected to the medical instrument body, and wherein the component is made from a material which changes color upon contact with fluid.

It is also an object of the present invention to provide a medical instrument wherein the component is a handle trigger or an actuator mechanism.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 8 and 9 show an alternate embodiment of a label in accordance with the present invention, wherein FIG. 8 shows a detailed plan view of the label while FIG. 9 shows a cross sectional view along the line 9-9 of FIG. 8.

FIGS. 11 and 12 show an alternate embodiment of a label utilized in accordance with the present invention, wherein FIG. 11 is a front plan view of the label and FIG. 12 is a cross sectional view along the line 12-12 of FIG. 11.

FIGS. 13 and 14 show yet another embodiment of a label for use in accordance with the present invention, wherein FIG. 13 is a front plan view of the label and FIG. 14 is a cross sectional view along the line 14-14 of FIG. 13.

FIGS. 37, 38, 39 and 40 are various views showing a label for utilization in identifying usage and/or reprocessing of a medical instrument, wherein FIG. 37 is a perspective view of the label, FIG. 38 is a cross sectional view along line 38-38 of FIG. 37, FIG. 39 shows the label after usage or exposure to reprocessing and FIG. 40 shows the label in its initial condition.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Since it is necessary to understand the underlying techniques currently employed in reprocessing medical instruments to gain a complete understanding of the present invention, the following discussion presents an overview of the techniques currently employed in the processing of medical instruments. Reprocessing generally relates to the preparation of medical instruments for further use. In particular, the preparation is commonly applied to single-use medical instruments and involves two major steps. The first is the cleaning stage and involves the removal of any foreign material from an item during reprocessing. The second step is sterilization and involves killing any living material, namely, any bacteria or virus, that could potentially contaminate a medical instrument.

Regardless of the reprocessing indicator technique employed in accordance with the present invention, it must fulfill certain criteria. In particular, the indicator technique must be applicable to a variety of single-use medical instruments, which vary in function, shape and size. The presence and location of the indicator should be known only to trained employees of the original manufacturer such that the original manufacturer may readily identify these items when they are returned based upon failures. In accordance with a preferred embodiment, it is contemplated neither the hospital staff nor administration should be aware of the indicator. The indicator could also be readily discernable to all hospital medical staff where such identification is desired. As medical instruments are commonly subjected to gamma radiation, the indication method employed in accordance with the present invention must be immune to gamma radiation and the indicator must be safe to any person in contact with the medical instrument during any part of the device's life. Further, the indicator should not surpass a critical level of bio-burden so as to not prevent effective sterilization levels being achieved and the indicator must be cost effective.

Figure 1:
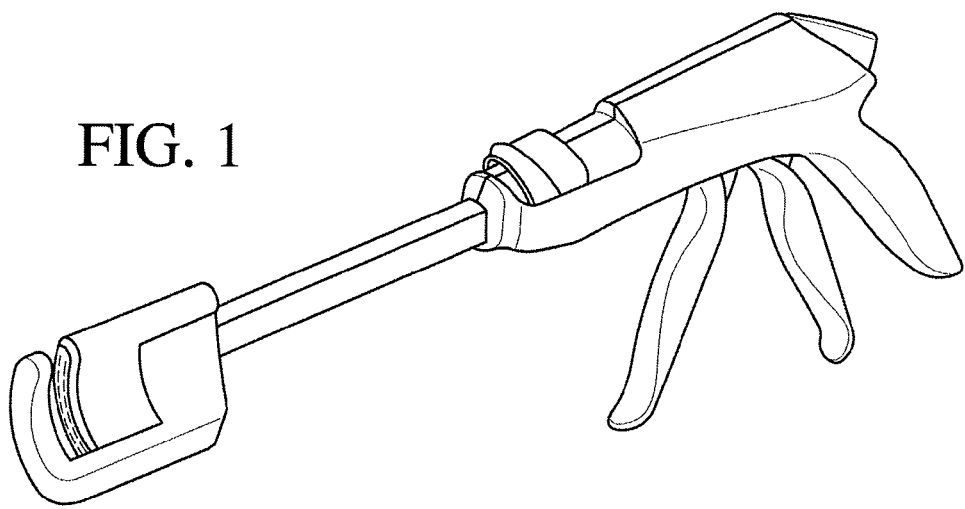
FIG. 1 is a perspective view of a medical instrument, in particular, a surgical stapler, as utilized in a traditional manner.
Figure 2:
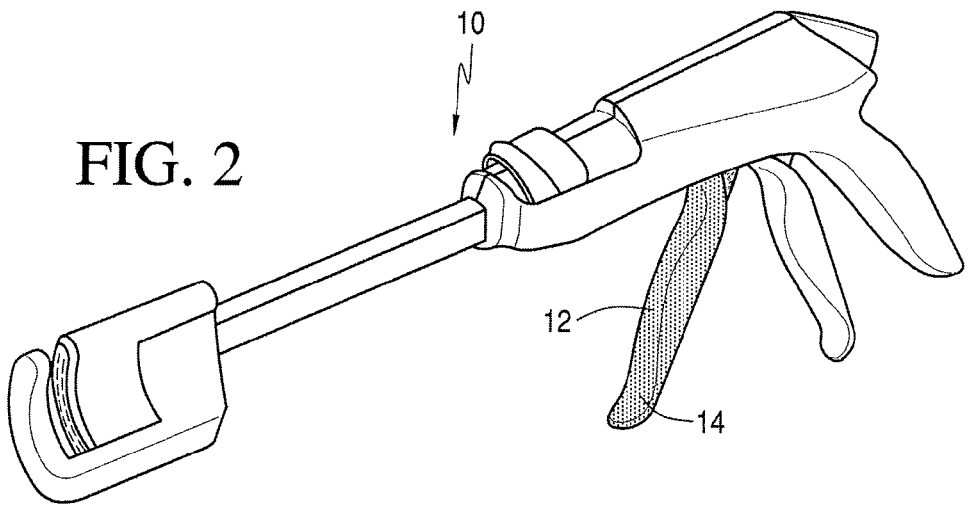
FIGS. 2 and 3 are alternate embodiments of a surgical stapler utilizing indicator inks in accordance with the present invention.
Figure 3:
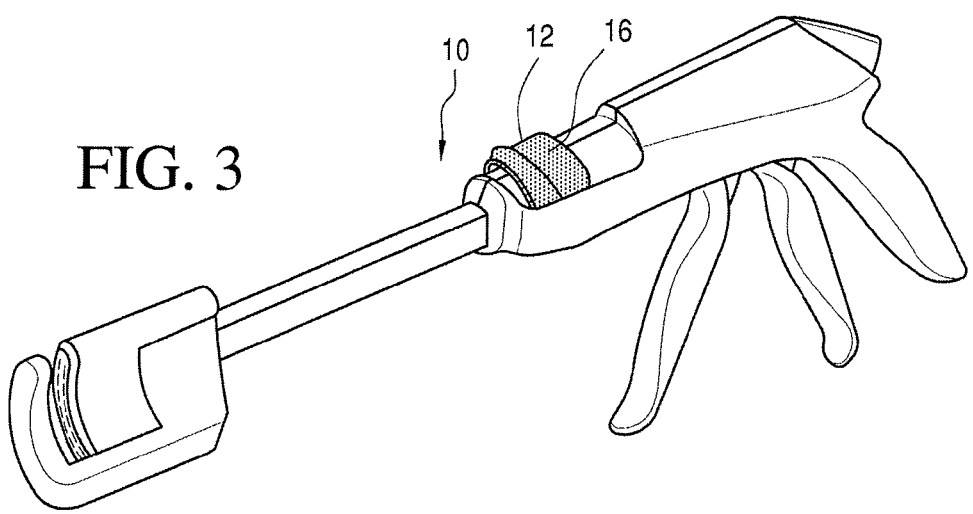
Figure 4:
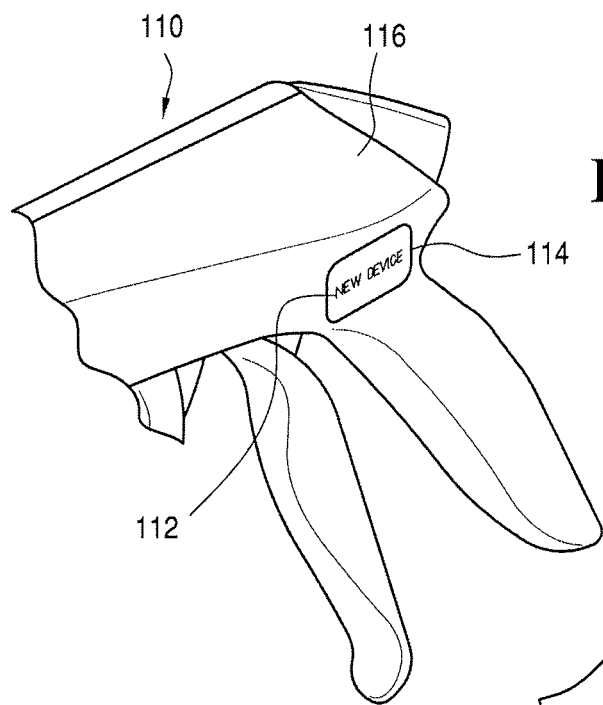
FIG. 4 is a perspective view of a label applied to the handle portion of a surgical stapler in accordance with the present invention.
Figure 5:
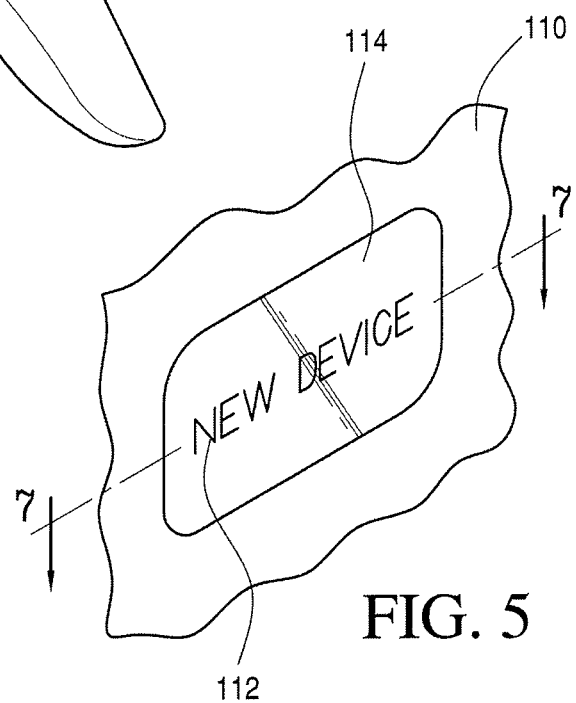
FIG. 5 is a detailed perspective view of the label of FIG. 5 prior to exposure to fluids and/or solvents.
Figure 6:
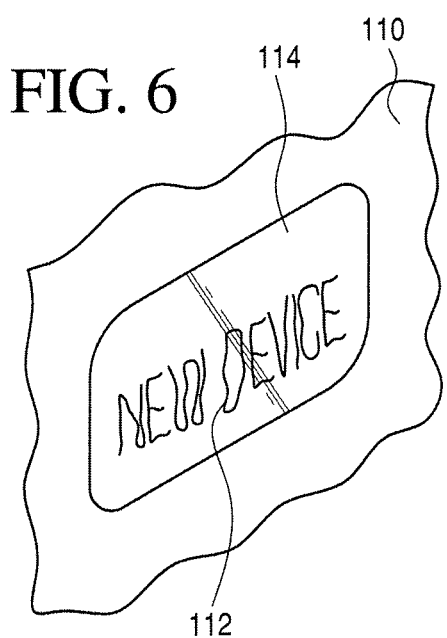
FIG. 6 is a detailed perspective view of the label of FIG. 5 after exposure to fluids and/or solvents.
Figure 7:
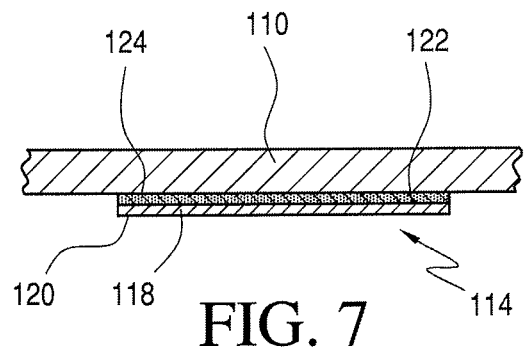
FIG. 7 is a cross sectional view of the label shown with reference to FIG. 5.

In accordance with a first embodiment, and with reference to FIGS. 2 and 3, water sensitive ink 12 is incorporated into the material composition of a component of the medical instrument 10. The water sensitive ink 12 changes color upon exposure to liquid. The ink 12 is preferably mixed with a polymer prior to molding the medical instrument component. The water sensitive ink 12 then becomes integral with the component of the medical instrument 10.

It is contemplated the water sensitive ink 12 is utilized in conjunction with a major component of the medical instrument (for example, the trigger handle 14 of a surgical stapler 10 as shown with reference to FIG. 2 or the actuation mechanism 16 as shown with reference to FIG. 3). By only having a component of the medical instrument 10 known to the manufacturer change color, the reprocessor may be unaware of the color change. That is, the reprocessor will not know the desired color of the trigger handle or actuation mechanism. In contrast, the water sensitive ink could be used as an inserted component of the medical instrument that becomes a part of the medical instrument at some time during assembly of the medical instrument.

In accordance with another embodiment, and with reference to FIGS. 4 to 7, a film label 114 printed with water (or other solution) soluble inks 112 is employed to provide an indication of reuse or reprocessing of a medical instrument 110 to a subsequent user of that same medical instrument 110. More particularly, the film label 114 printed with water (or other solution) soluble inks 112 is applied to the medical instrument 110 during assembly and prior to use of the medical instrument 110.

The embodiment shown with reference to FIGS. 4 to 7 provides an indication of prior use by incorporating the water-soluble inks 112 into the medical instrument 110 by applying the water-soluble inks 112 upon a label 114 that is applied to the handle or shroud 116 of the medical instrument 110 along a location that preferably remains outside of a patient during use.

In accordance with a preferred embodiment, the water-soluble ink 112 is chosen such that it becomes adulterated when exposed to typical solutions used in medical instrument cleaning processes such as water, enzymatic or alkaline detergents, liquid sterilants (such as Cidex, marketed by Johnson & Johnson Advanced Sterilization Products or other liquid).

The label 114 used in accordance with a preferred embodiment and as shown with reference to FIGS. 4 to 7, is protected during initial use by printing the water-soluble ink 112 on the hidden surface of a clear film 118 in a reverse manner such that it is readily readable or recognizable from the exposed side of the label 114. More particularly, the label 114 includes a clear film 118. The clear film 118 is provided with a first surface 120 that is exposed for viewing when the label 114 is applied to the medical instrument 110 and a second surface 122 the faces the medical instrument 110 (and is therefore hidden) once applied to the medical instrument 110. The water-soluble ink 112 is printed upon the second surface 122. The label 114 is further provided with an adhesive layer 124. The adhesive layer 124 is applied to the second surface 122 and is directly secured to the medical instrument 110 upon assembly thereof.

Figure 8:
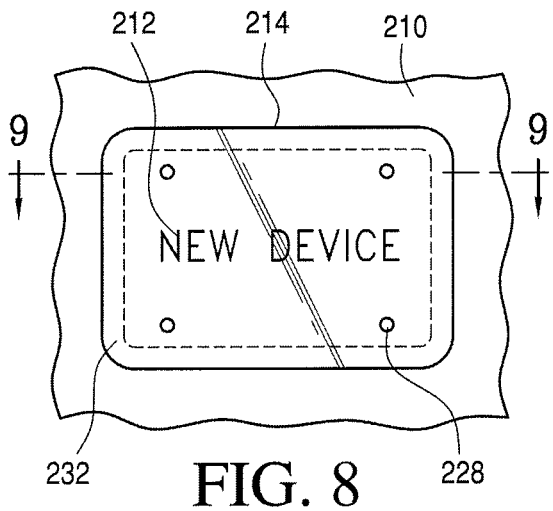
Figure 9:
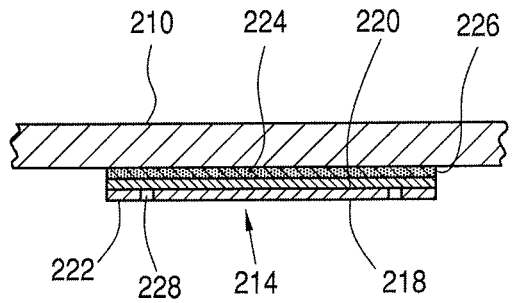

In accordance with another embodiment as shown with reference to FIGS. 8 and 9, the label 214 includes a clear film 218 provided with a first surface 220 that is exposed when the label 214 is applied to the medical instrument 210 and a second surface 222 that faces the medical instrument 210 (and is therefore hidden) once applied to the medical instrument 210. The water-soluble ink 212 is printed upon the second surface 222. An adhesive backed substrate 226 such as film, paper, paperboard, foil, or thin metal plate is laminated to the second surface 222 of the clear film. The adhesive layer 224 of the adhesive backed substrate 226 is directly secured to the medical instrument 210 upon assembly thereof.

When the label 214 is applied to a medical instrument 210, liquid coming into contact with the label 214 is allowed to flow under the clear film 218 making contact with the water-soluble ink 212 printed upon the second surface 222 by flowing along the back (or second) surface 222 of the clear film 218. The flow of liquids into contact with the water-soluble ink 212 may be accomplished in a number of manners as shown with reference to FIGS. 4 to 15. In accordance with the embodiment shown with reference to FIGS. 5, 6 and 7, the fluid is simply allowed to flow between the clear film 118 and the medical instrument 110, and into contact with the indicator ink 112.

Figure 10:
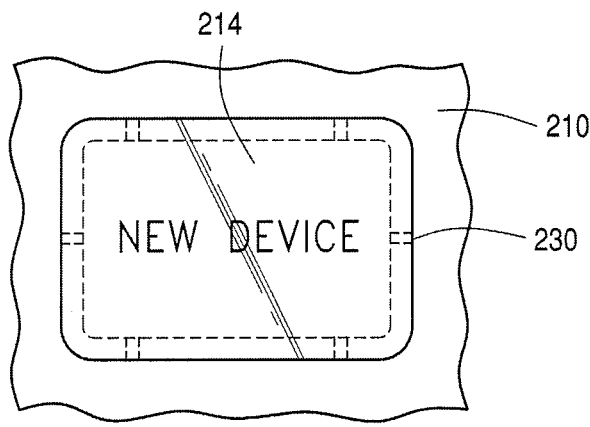
FIG. 10 is a front plan view of a label in accordance with an alternate embodiment of the present invention.

Referring to the embodiment shown with reference to FIGS. 8, 9 and 10, the top clear film 218 is applied to the adhesive backed substrate 226 as shown in accordance with the embodiment of FIGS. 8 and 9, using adhesive, or a heat seal pattern, 232 around the perimeter of the top clear film 218 and perforations or holes 228 (see FIGS. 8 and 9) or laterally oriented channels 230 (see FIG. 10) are cut into the top clear film 218 providing a passageway for liquid to make its way to the second surface 222 of the clear film 218 within the area defined by the perimeter bonding material. In this manner liquids and/or solutions are permitted to flow under the top clear film 218 and be caught for a period under the clear film 218 along the second surface 222 to allow enough time to activate the water-soluble ink 212 and disrupt its visual integrity.

Figure 13:
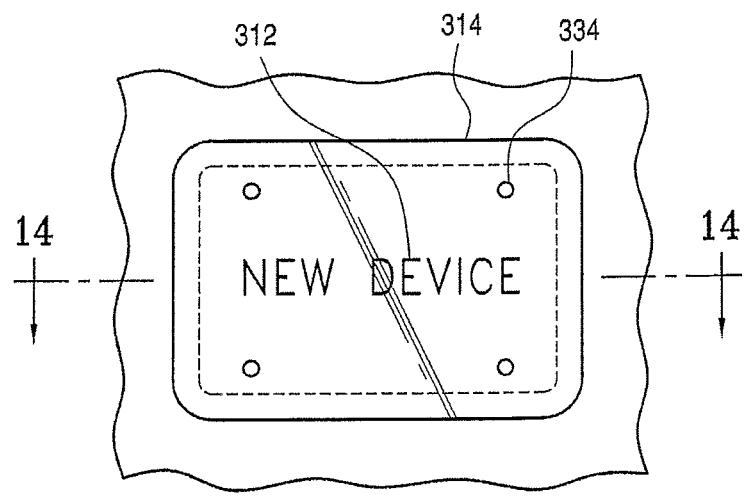
Figure 14:
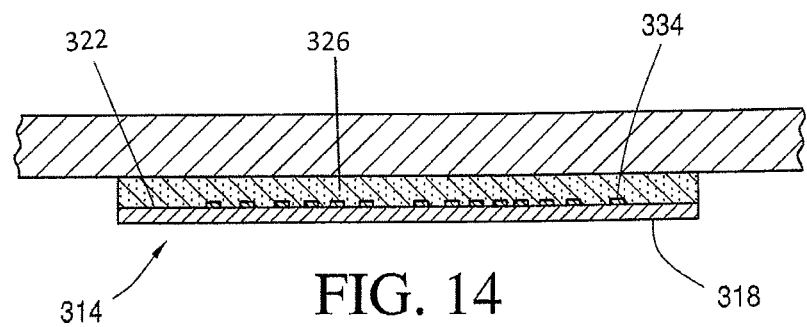

Referring to FIGS. 13 and 14, it is further contemplated the label 314 is constructed such that the flow of liquid into contact with the water soluble ink 312 along the second surface 322 of the clear film 318 may be accomplished through channels 334 formed in bonding points between the top clear film 318 and a secondary backing layer 326 (or the medical instrument in accordance with an alternate embodiment) such that solutions can flow under the top clear film 318 from the edges thereof, through the unbonded points or channels 334, and into contact with the water soluble ink 312.

Figure 11:
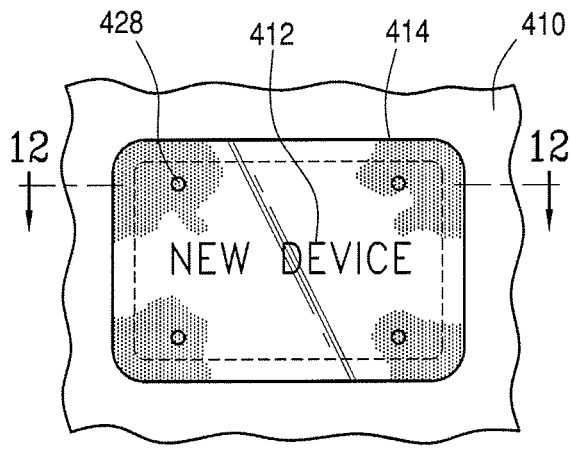
Figure 12:
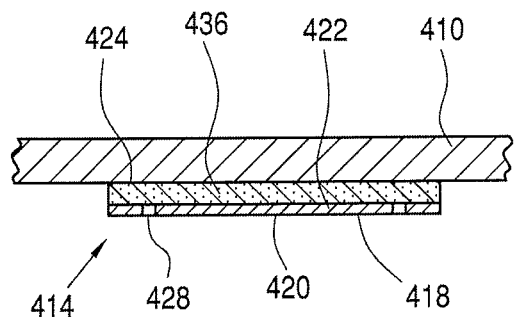

In addition, and in accordance with a preferred embodiment of the present invention as shown with reference to FIGS. 11 and 12, the label 414 may include an absorbent secondary backing layer 436 under the top clear film 418 top such that when a cleaning solution flows between the backing layer 436 and the top clear film 418 (for example, via holes 428 formed in the top clear film 418), and begins to solubilize the water soluble inks 412, they are absorbed into the backing layer 436, such as could be done with an absorbent paper, leaving a visible evidence of their form or presence in the form of a stain.

More particularly, the label 414 of the embodiment shown with reference to FIGS. 11 and 12 includes a top clear film 418 provided with a first surface 420 that is exposed for viewing when the label 414 is applied to the medical instrument 410 and a second surface 422 the faces the medical instrument 410 (and is therefore hidden) once applied to the medical instrument 410. The water-soluble ink 412 is printed upon the second surface 422. The backing layer 436 is composed of an absorbent paper that is laminated to the second surface 422 of the top clear film 418. The adhesive layer 424 of the backing layer 436 is directly secured to the medical instrument 410 upon assembly thereof.

Figure 15:
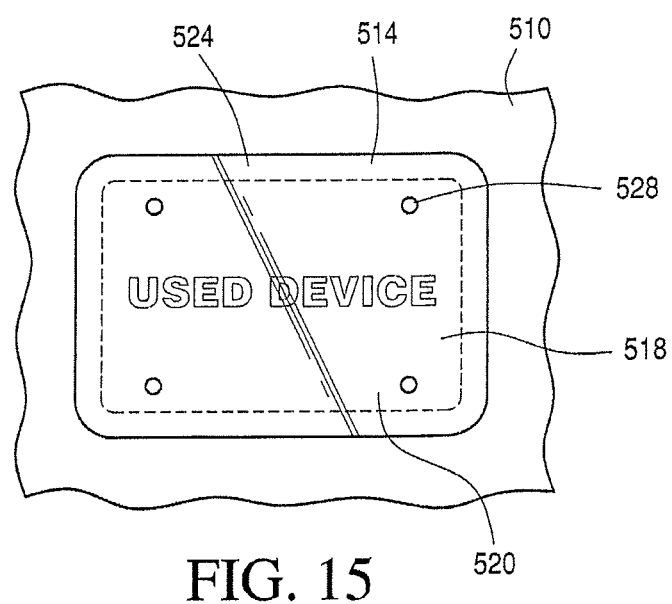
FIGS. 15, 16 and 17 show various views in accordance with an alternate embodiment of the present invention.
Figure 16:
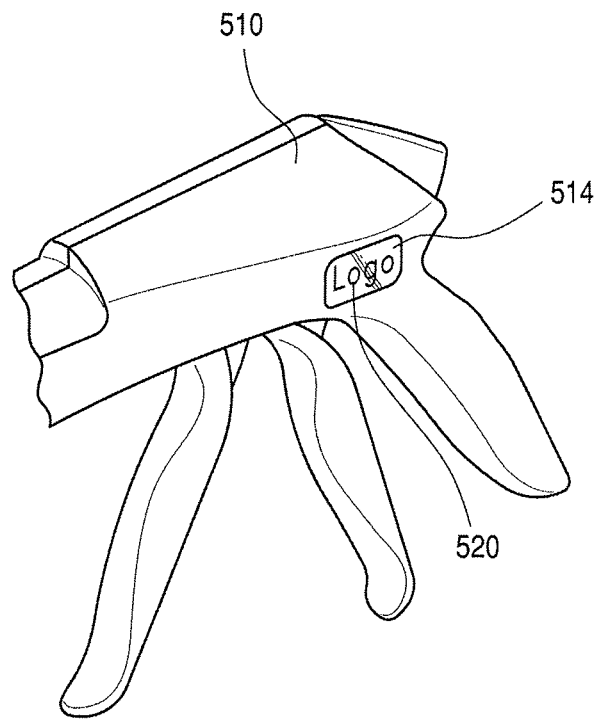
Figure 17:
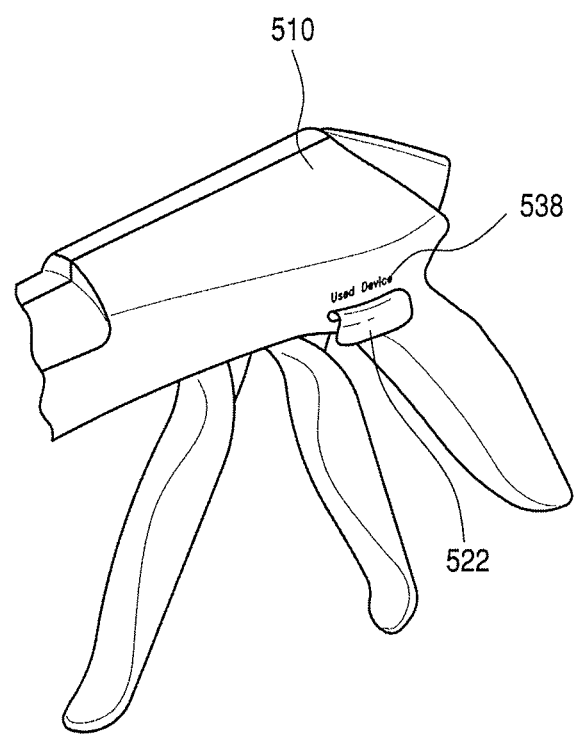

In accordance with yet another embodiment of the present invention and with reference to FIGS. 15, 16 and 17, a medical instrument 510 is printed with a message such as USED DEVICE or REPROCESSED 538 and these words are covered with an opaque label 514 such that it is no longer visible. The label 514 may be blank or contain the original device manufacturer's company name logo or product trademark or other graphics. The bonding of this label 514 to the medical instrument 510 is preferably accomplished with adhesives that are weakened when exposed to cleaning processes (exposed preferably via holes 528 formed in the label 514) used by reprocessors but not in the original manufacturing process such as water cleaning enzymatic or alkaline detergents or liquid sterilants such as Cidex, from Johnson & Johnson Advanced Sterilization Products. This would result in a labeled medical instrument 510 that when reprocessed following an initial use would result in the label 514 becoming detached to varying degrees (or completely) revealing the underneath hidden text, message and/or graphics on the medical instrument to alert subsequent users of the medical instrument that it has been reprocessed.

More particularly, the opaque label 514 is constructed in a manner similar to the label 114, 214 disclosed with reference to the embodiments of FIGS. 4 to 14, although the label 514 of this embodiment is composed of an opaque top film 518 (as opposed to the clear film of the labels employed within reference to FIGS. 4 to 14). The top film 518 includes a first surface 520 which is exposed for viewing upon application to the medical instrument 510 and a second surface 522 which faces the medical instrument 510 (and is therefore hidden) upon application to the medical instrument 510. The top film 518 is provided with adhesive 524 along the second surface 522 for bonding the label 514 to medical instrument 510.

In order to ensure penetration of fluid solvent to the second surface 522 for interaction with the adhesive 524 in a manner releasing the label 514 from the medical instrument 510 for exposing the markings 538 applied to the surface of the medical instrument 510, adhesive 524 is applied only along the perimeter of the top film 518 and perforations, holes 528 or laterally oriented channels (see FIGS. 10, 13 and 14) are cut into the top film 518 providing a passageway for liquid to make its way to the second surface 522 of the top film 518 within the area defined by the perimeter bonding material. In this manner liquids and/or solutions are permitted to flow under the top film 518 and be caught for a period under the top film 518 along the second surface 522 to allow enough time to interact with the adhesive 524 and disrupt the bond between the medical instrument 510 and the top film 518.

Figure 18:
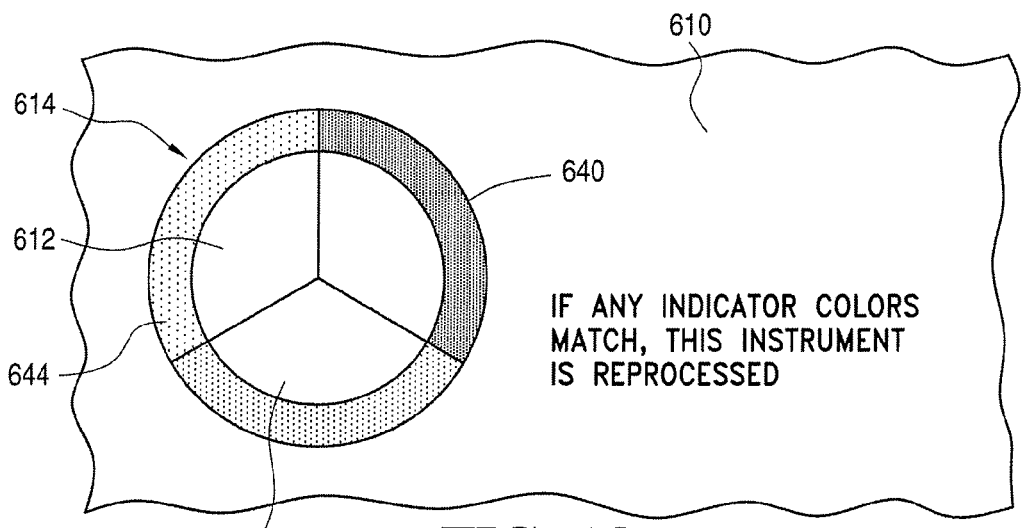
FIGS. 18, 19 and 20 show various views of an indicator symbol in accordance with an alternate embodiment of the present invention.
Figure 19:
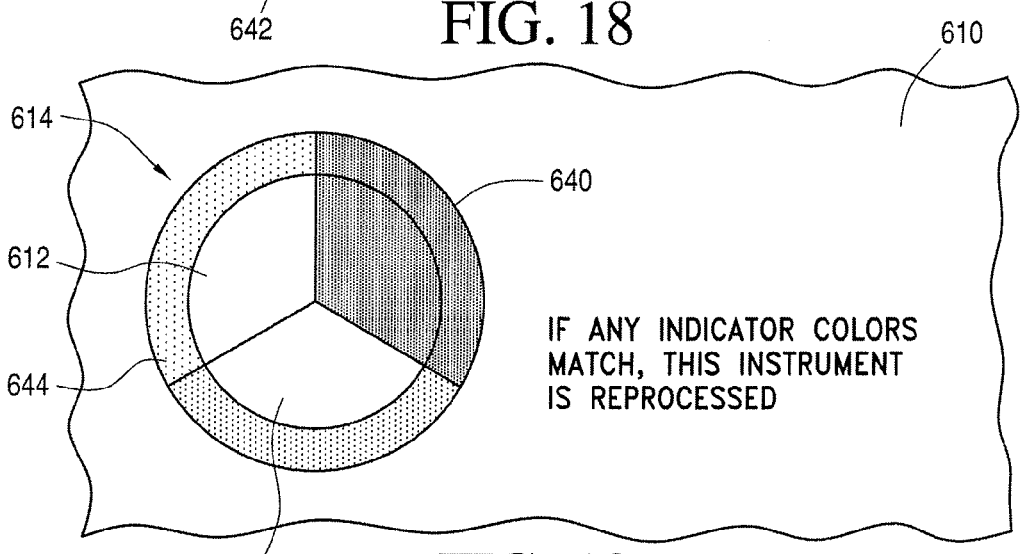
Figure 20:
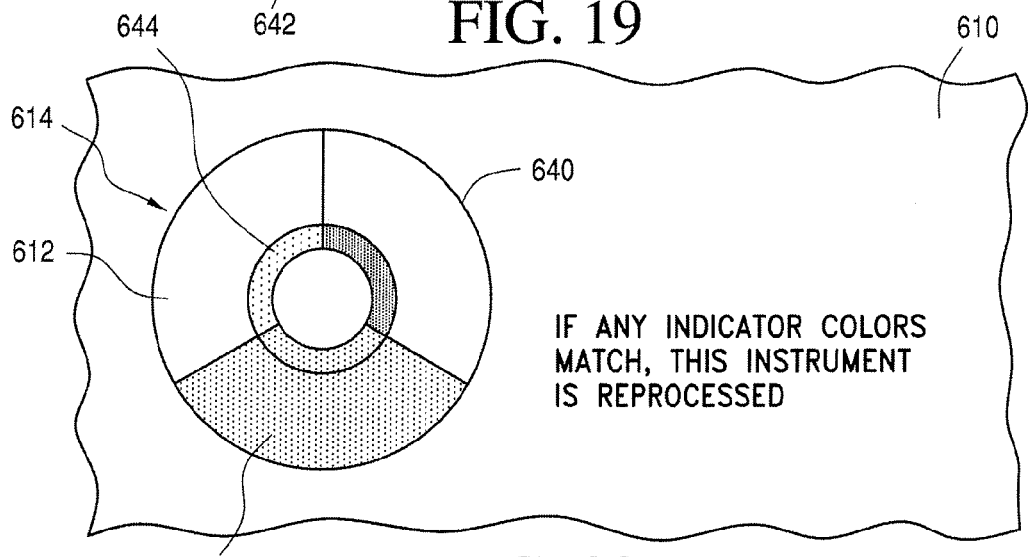

In accordance with yet another embodiment, and with reference to FIGS. 18, 19 and 20, a printed indicator label 614 is utilized to indicate various exposure types that reprocessed medical instruments 610 might be confronted with during the reprocessing methods. In accordance with this embodiment, the label 614 is composed of an indicator symbol 640 printed upon the surface of the medical instrument 610. Indicator symbol 640 is composed of reactive ink 612 such that the reactive ink 612 turns color when exposed to various processing environments, such as, but not limited to, water, Cidex, soaking enzymatic or alkaline detergents or various sterilization methods of use, such as, but not limited to, ethylene oxide gas, hydrogen peroxide plasma, steam sterilization, etc.

While the indicator symbol 640 is disclosed herein as being printed directly on the medical instrument, it is contemplated the indicator symbol may be printed upon or otherwise integrated into an adhesive backed printed label which is secured to the body of the medical instrument. In accordance with a preferred embodiment, the indicator symbol 640 takes the form of a circle subdivided into pie shaped wedge sections 642 with each section printed with a unique reactive ink 612 for reacting to specific exposure of processing fluids to indicate to which processing fluids the medical instrument has been exposed. Each of the pie shaped wedge sections 642 of the circle would be for unrelated process indicator reactive inks 612 and so on until the indicator pie shaped wedge sections 642 are all used. The reactive inks 612, when exposed to the environmental condition or process of chemical exposure, turn color to indicate that the medical instrument 610 saw that particular condition in its life.

It is further contemplated that it is desirable to provide a color scale 644 near each indicator reactive ink 612 that shows a user of the present invention what the expected color is when it does turn color. In accordance with a preferred embodiment, the scale is a border around the indicator symbol 640 (see FIGS. 18 and 19), or in its center (see FIG. 20), such that it sections a line with the appropriate indicator reactive ink 612 to provide a before and after visual queue. Further instructions may be printed that instruct users that the medical instrument has been reprocessed or reused if the indicator ink matches the preprinted color scale.

Figure 21:
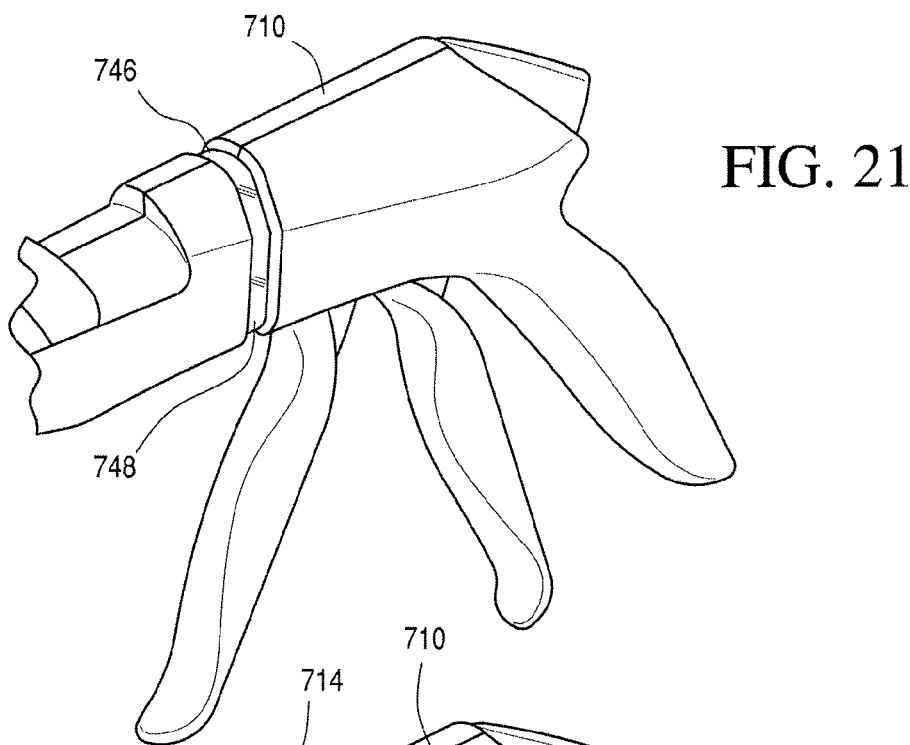
FIGS. 21, 22 and 23 show perspective views of a label utilized along the seam of a medical instrument in accordance with an alternate embodiment of the present invention.
Figure 22:
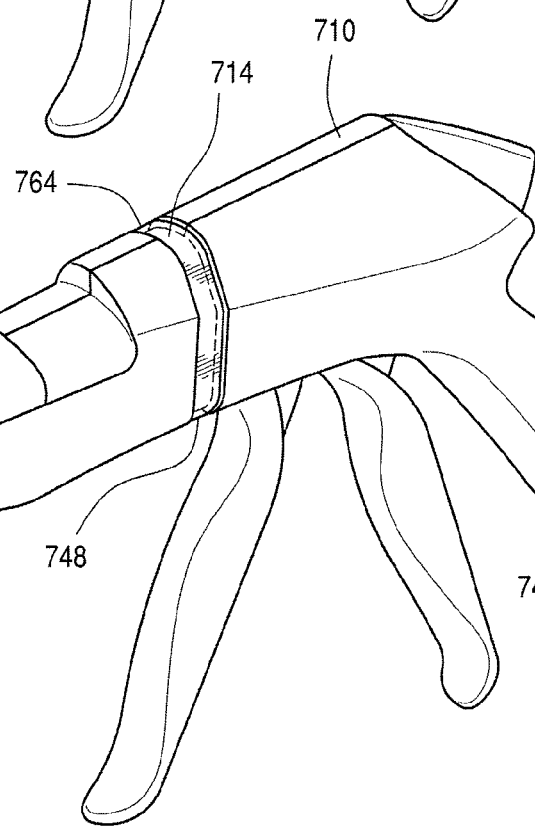
Figure 23:
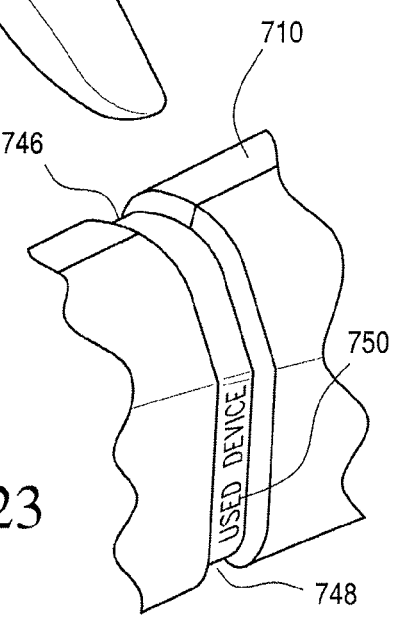

It is further contemplated the actual shape of the indicator symbol may be other than a circle. As such, the indicator symbol may be of various shapes determined to be conducive to the particular device. In addition, it is contemplated the various indicator inks and specific markings may be varied to suit the specific application for which the medical instrument is intended to be used and environments to which the medical instrument may be exposed In accordance with yet a further embodiment, and with reference to FIGS. 21, 22 and 23, a label or band 714 is positioned on or around a seam 746 of an assembled medical instrument 710 during the assembly process such that it falls off when a reprocessor attempts to disassemble the medical instrument 710 during the reprocessing thereof. Many medical instruments 710 are assembled with two or more pieces allowing for the opportunity to apply a label or band 714 around the two pieces such that the label or band 714 adheres to itself but not the medical instrument housing itself.

The label or band 714 is applied in a recessed area 748 provided that it does not and cannot be removed intact. Once broken or cut the label or band 714 falls off completely thus removing any desired information so as to differentiate an original manufacturer's medical instrument 710 from one disassembled and reworked (see FIG. 23). It is contemplated the label or band 714 may be of a heat shrink type material or of a paper or film material that is wrapped and sealed to itself with heat or adhesive. It may further be desired to print a different message or text or symbol 750 to the medical instrument 710 along the seam 746 which is covered by the label or band 714 such that when it is removed the underlying graphics image message 750 is revealed.

Figure 24:
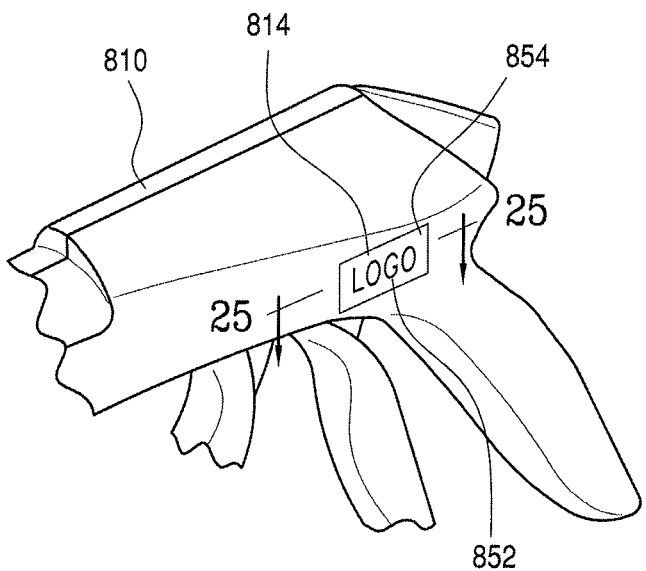
FIGS. 24, 25 and 26 show yet another embodiment of an indicator mechanism for utilization in accordance with the present invention.
Figure 25:
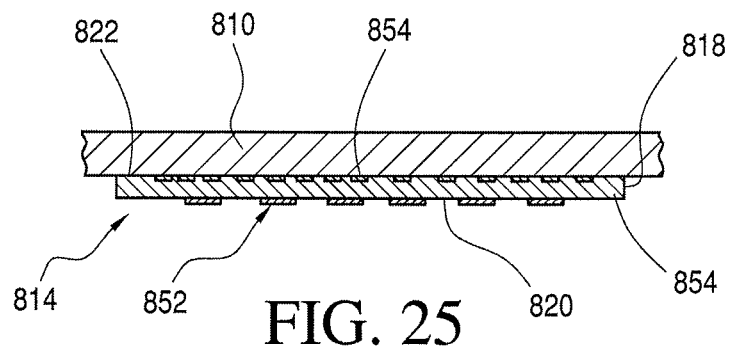
Figure 26:
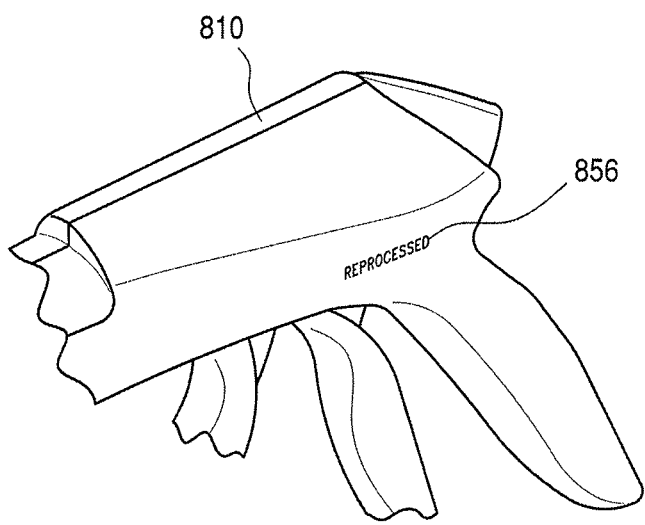

In accordance with yet another embodiment as disclosed with reference to FIGS. 24, 25 and 26, a label 814 composed of trademarks and other company graphics are printed on a medical instrument 810 using soluble inks that become degraded by exposure to cleaning processes used in reprocessing medical instruments 810. In this manner a reprocessed medical instrument 810 would result in a medical instrument 810 without its original manufacturer's name on it. In accordance with a preferred embodiment, the printing is layered such that the original medical instrument 810 shows a top printing layer 852 of the medical instrument trademark on top of an opaque background 854 printed using soluble inks and then underneath a third hidden layer (or permanent ink layer) 856 using permanent inks with a message such as REPROCESSED or NOT A J&J PRODUCT (see FIG. 26). When reprocessed, the top two soluble ink layers 852, 854 are removed exposing the third permanent ink layer 856.

More particularly, the label 814 for such an embodiment includes a clear film 818 including a first surface 820 exposed to the environment once the label 814 is applied to the medical instrument 810 and second surface 822 facing the medical instrument 810 (and therefore hidden) once the label 814 is applied to the medical instrument 810. The trademarks and other company graphics 852, 854 are printed on the first surface 820 of the label 814 that becomes degraded by exposure to cleaning processes used in reprocessing medical instruments 810. The second surface 822 of the label 814 is printed with a warning message, for example, REPROCESSED, such that once the trademark or other company graphics 852, 854 printed upon the first surface 820 are degraded by exposure to cleaning processes used in the reprocessing of the medical instrument 810, the warning message is exposed (see FIG. 26).

Figure 27:
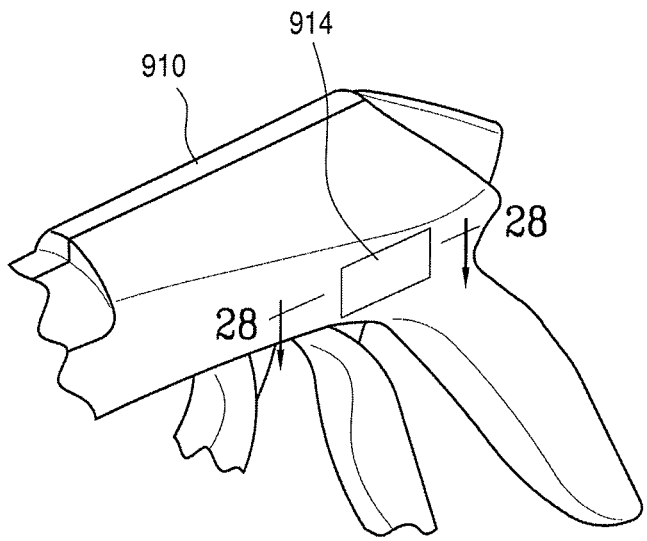
FIGS. 27, 28 and 29 show an indicator symbol which dissolves upon exposure to fluids and/or solvents for indicating use of a medical instrument in accordance with the present invention.
Figure 28:
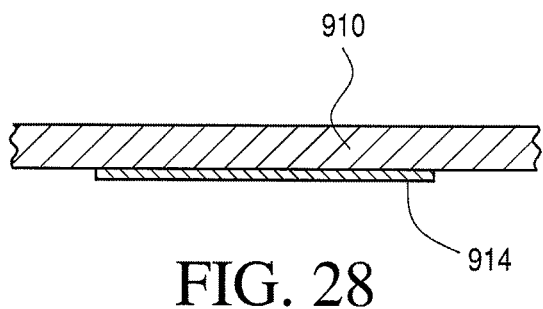
Figure 29:
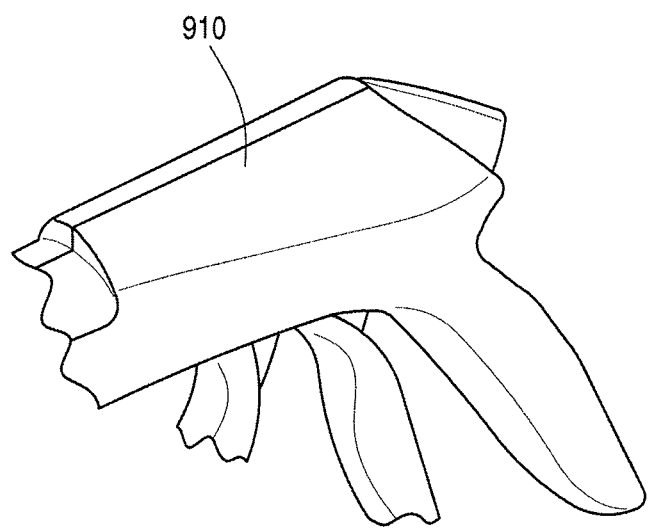

In accordance with another embodiment, and with reference to FIGS. 27, 28 and 29, an invisible unique coating or label 914 is applied to an area of a single-use medical instrument 910 such that it is readily detectable using available analytical equipment. The coating 914 contains trace amounts of uniquely detectable chemicals or compounds such that when present they can be detected and when specific medical instruments 910 are cleaned, decontaminated and resterilized the chemical coating is removed by this reprocessing technique. Such reprocessing techniques might include water washing, scrubbing, hot water washing, decontaminated ultrasonic cleaning with detergent, etc.

Following such a cleaning process as shown with reference to FIG. 29, the coating 914 is not detected, thus differentiating medical instruments 910 that have been reprocessed versus those which have not. This is especially important during complaint analysis and review of failed devices in order to clearly identify reused medical instruments to avoid their entry into the complaint system.

It is contemplated the specific coatings 914 used in accordance with this embodiment would be of a composition that is soluble in water or other specific solutions that a used medical instrument 910 would be subject to in a cleaning process. They could include DNA containing solutions, monoclonal antibodies or other specialized chemicals that are considered safe for human contact and that provide a unique fingerprint for later analysis so that there is no question as to their origin or when they are and are not present.

Figure 30:
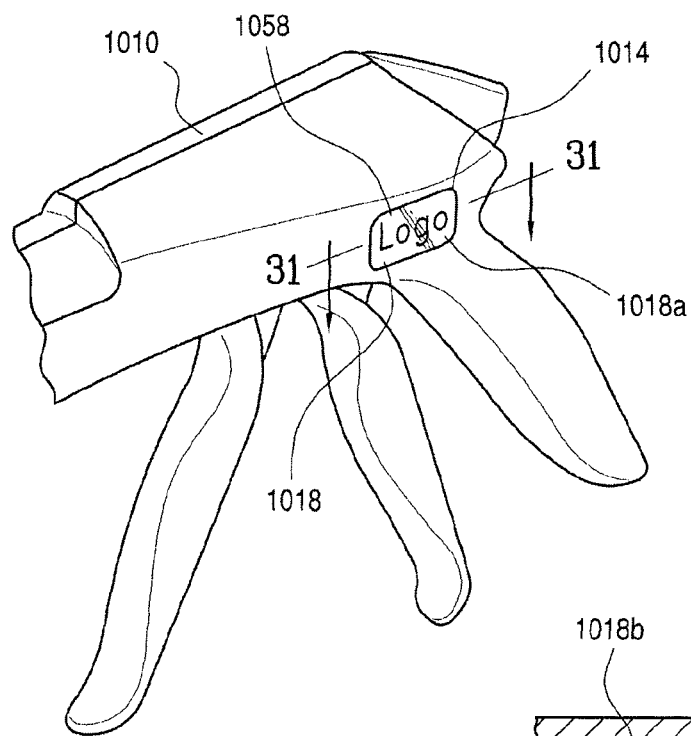
FIGS. 30, 31 and 32 show a dual film label wherein the top film is removed upon exposure of the label to fluids and/or solvents.
Figure 31:
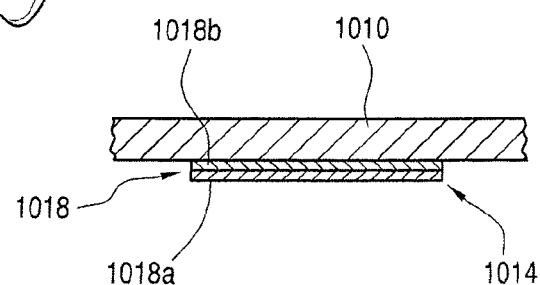
Figure 32:
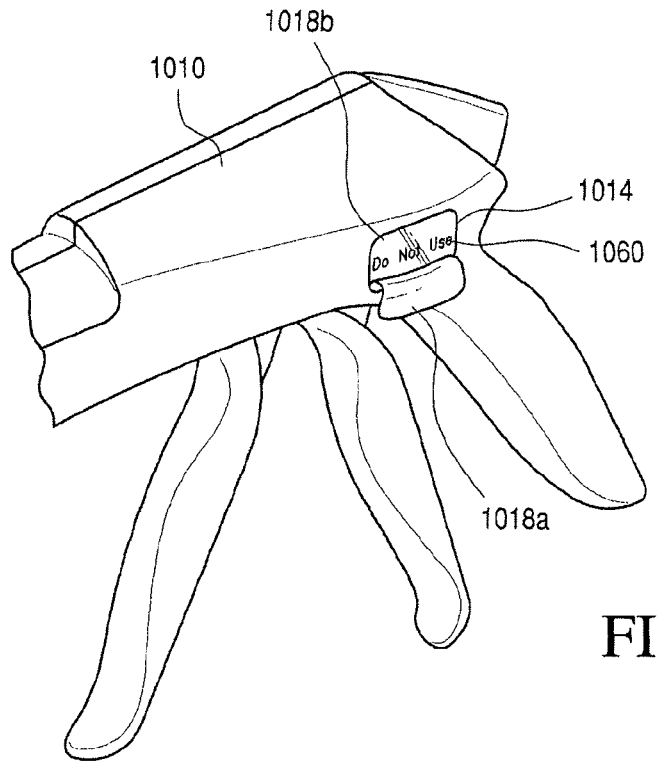

In accordance with another embodiment, and with reference to FIGS. 30, 31 and 32, the medical instrument 1010 includes a label 1014 comprising a two layer film 1018 laminated together with water (or solution) soluble adhesive such that when exposed to a cleaning process involving dipping, soaking or other exposure to liquids typically used in cleaning processes, the top layer 1018a delaminates from the base layer 1018b. The top layer 1018a is provided with product specific label graphics 1058 on it such that when it detaches it is easily recognizable by those performing subsequent procedures with the same medical instrument 1010 that it has been previously used. This is done by either providing no graphics on the base layer 1018b of the label 1014 or providing a different graphic 1060, such as REUSED or REPROCESSED DEVICE or DO NOT USE printed on the base layer 1018b that becomes exposed upon cleaning in solutions (see FIG. 32). In this manner, it becomes readily apparent to the surgeon performing the surgical procedure that the medical instrument 1010 had been used previously.

Figure 33:
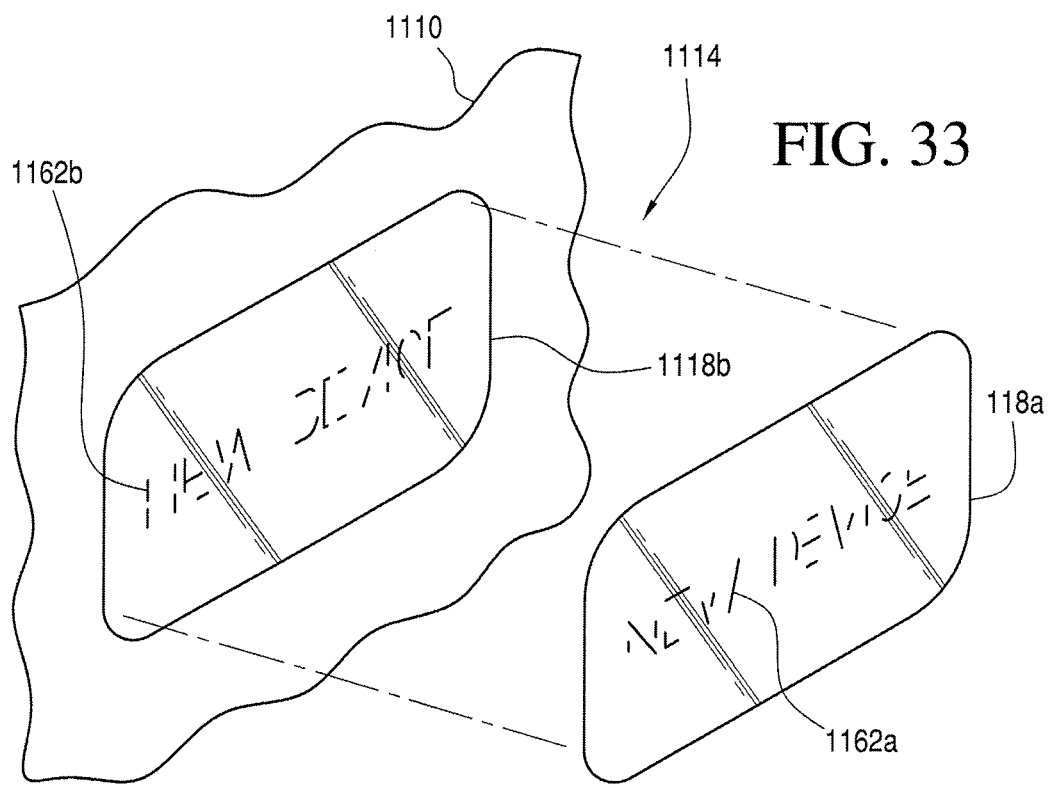
FIGS. 33 and 34 show another dual film label wherein optical interaction between the top film and the bottom film are utilized to achieve identification of prior usage or reprocessing of the medical instrument.
Figure 34:
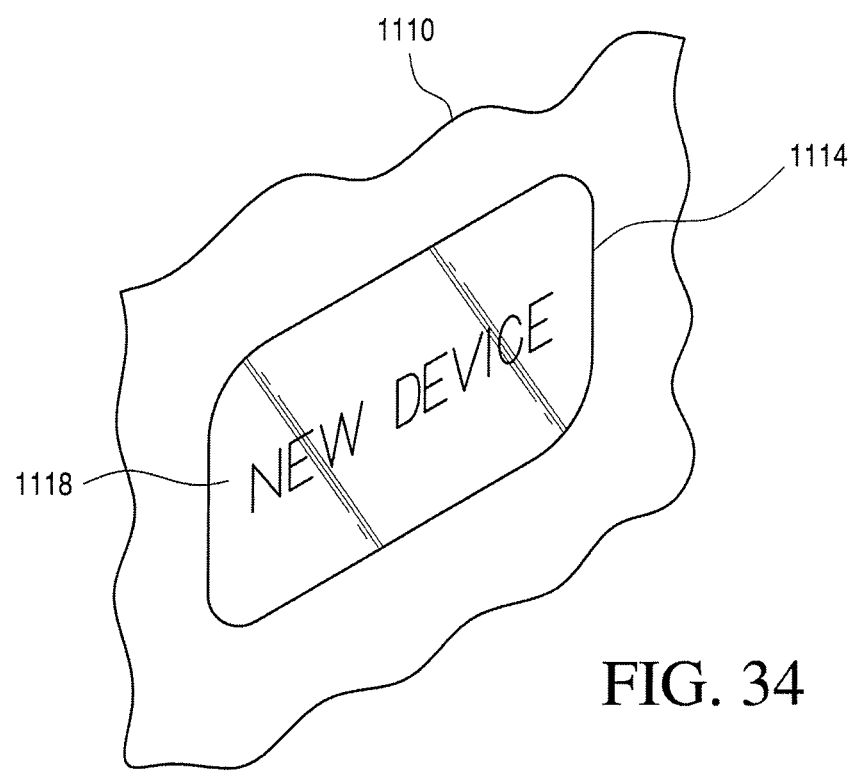

In accordance with an alternate embodiment as shown with reference to FIGS. 33 and 34, the medical instrument 1110 includes a label 1114 comprising a two layer film 1118 composed of a top layer 1118a and a base layer 1118b laminated together with water (or solution) soluble adhesive such that when exposed to a cleaning process involving dipping, soaking or other exposure to liquids typically used in cleaning processes, the top layer 1118a delaminates from the base layer 1118b. In contrast with the embodiment disclosed above with reference to FIGS. 30, 31, and 32, the top and base layers 1118a, 1118b of the label 1114 are combined to reveal a desired message using available "Optical Key" technologies, that is, where each of the top layer and base layer 1118a, 1118b distorts the intended image (see FIG. 33) but together they form a legible image (see FIG. 34) such as that offered by TrustCopy. This technology provides that the top layer 1118a and the base layer 1118b independently do not convey any recognizable text or other image, however, when laid one onto the other in a specific orientation and position the images of the top and base layers 1118a, 1118b align to produce a recognizable message in text or pictorial form, such as a product trademark or company logo or name (see FIG. 33). As a result, when the top layer 1118a falls off it no longer is recognizable that the medical instrument 1110 is one from the original manufacturer (see FIG. 34). It is contemplated this may be accomplished by printing partial aspects of the image 1162a, 1162b on each of the top layer and the base layer 1118a, 1118b so they fit together to form like an image puzzle. This would also make the label 1114 not easily reproduced, especially if the images 1162a, 1162b of the label 1114 are varied over time from batch to batch.

Figure 35:
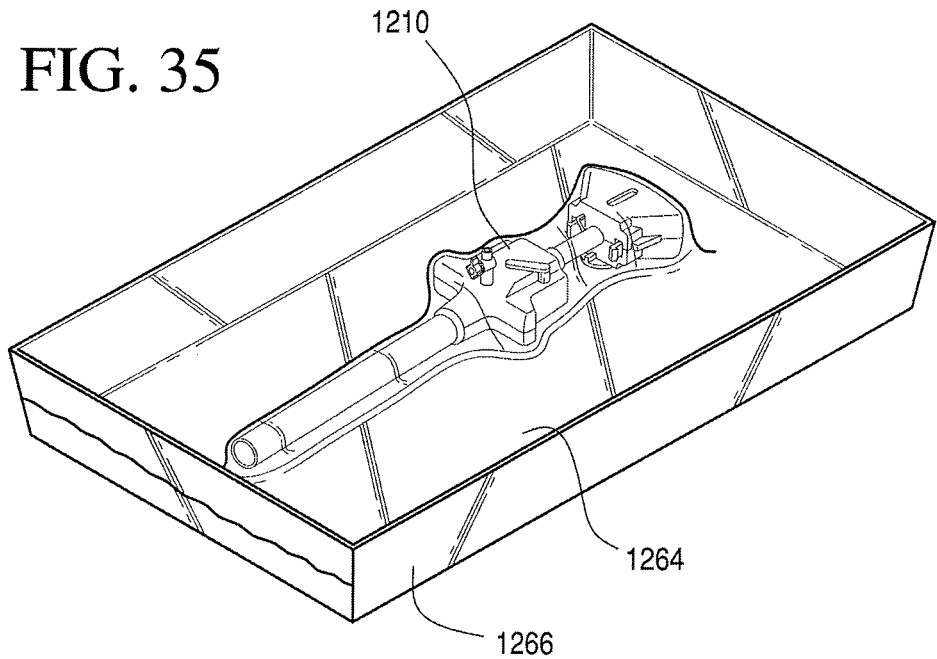
FIGS. 35 and 36 show yet another embodiment for indicating usage of a medical instrument in accordance with the present invention.
Figure 36:
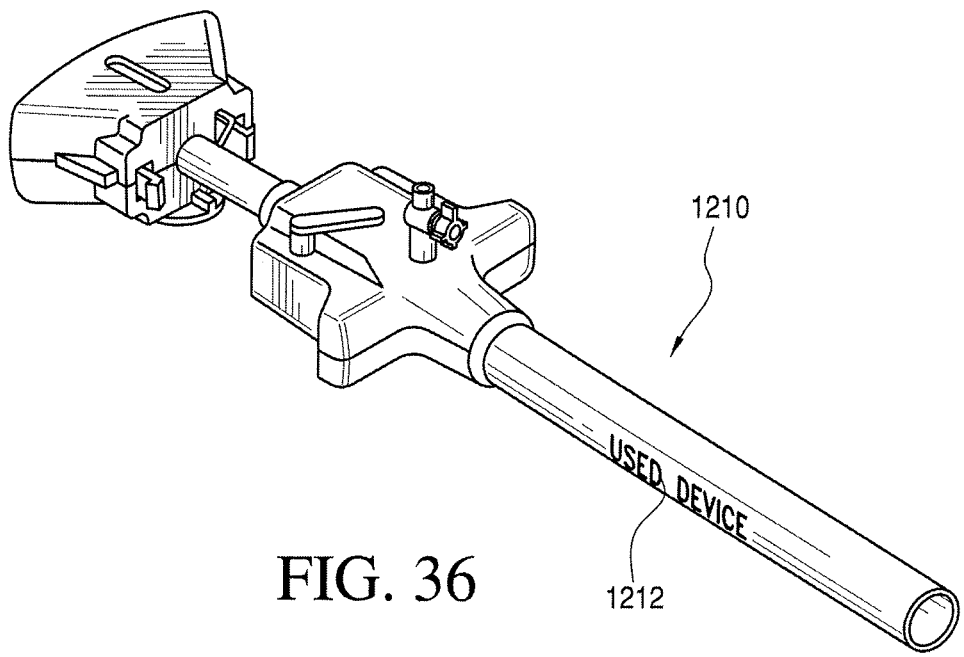

In yet another embodiment, and with reference to FIGS. 35 and 36, medical instruments 1210 are marked with permanent ink 1212 which changes color after a period of time following the removal of a protective film cover 1264. The amount of time would allow for normal use, for example, eight hours of surgery. It is contemplated the ink 1212 is used to convey a warning message. In accordance with a preferred embodiment, the film cover 1264 is connected to the medical instrument tray 1266 upon which the medical instrument 1210 lies in the packaging such that when the medical instrument 1210 is pulled from the medical instrument tray 1266 the film cover 1264 is retained on the medical instrument tray 1266 and removed from the medical instrument 1210 in a manner exposing the ink 1212 and starting the time until color change in message appearance (see FIG. 36). In choosing materials for construction of a medical instrument 1210 in accordance with this embodiment, it should be appreciated, the film/ink combination must survive sterilization, such as gamma radiation. This time based color change could be atmospheric vapor induced (for example, oxygen or carbon dioxide) or by light exposure (for example, UV or visible light).

In accordance with yet a further embodiment, and with reference to FIGS. 37, 38, 39 and 40, an absorptive material 1370 is attached to the medical instrument 1310 during the assembly process to allow for detection of prior use of the medical instrument 1310. The absorptive material 1370 is sensitive to specific substances such as carbon dioxide (for laparoscopic procedures), water or biological fluids. In the simplest case, the material could be paper with an ink marking 1312 (ink would migrate and distort the marking if in contact with fluids).

In accordance with a preferred embodiment, the absorptive material 1370 is trapped inside two clear flexible pieces of plastic 1372, 1374 allowing for clear visualization thereof. The two pieces of plastic 1372, 1374 are joined together in such a way as to create a pathway allowing fluids to migrate into contact with the absorptive material 1370. In accordance with a preferred embodiment, this pathway is created by ultrasonically welding the two pieces of plastic 1372, 1374 together around the periphery excluding a region. The unwelded region(s) 1376 would then function as the pathway for fluids. The trapped absorptive material 1370 is affixed to medical instruments 1310 using either an adhesive or second tack-welding process 1324 (or similar materials). During use, fluids (carbon dioxide, water and/or biological fluids) would contact the absorptive material 1370 either changing its color, shape, size or other feature (see FIG. 39). Subsequent sterilization would not affect the change. If the medical instrument 1310 were washed, the color would change also indicating prior use. Alternatively new medical instruments would be designed with a pocket in place for an absorptive material to be inserted during the assembly process.

Another method of detecting prior use of medical instruments is to have a coating of material sensitive to carbon dioxide applied to the medical instrument. Examples of appropriate materials can be found within patents, such as U.S. Pat. No. 4,728,499, which is incorporated herein by reference, and generally constitute a material that changes color during and after exposure. The material is applied to the medical instrument during the assembly process using an adhesive or friction.

Figure 41:
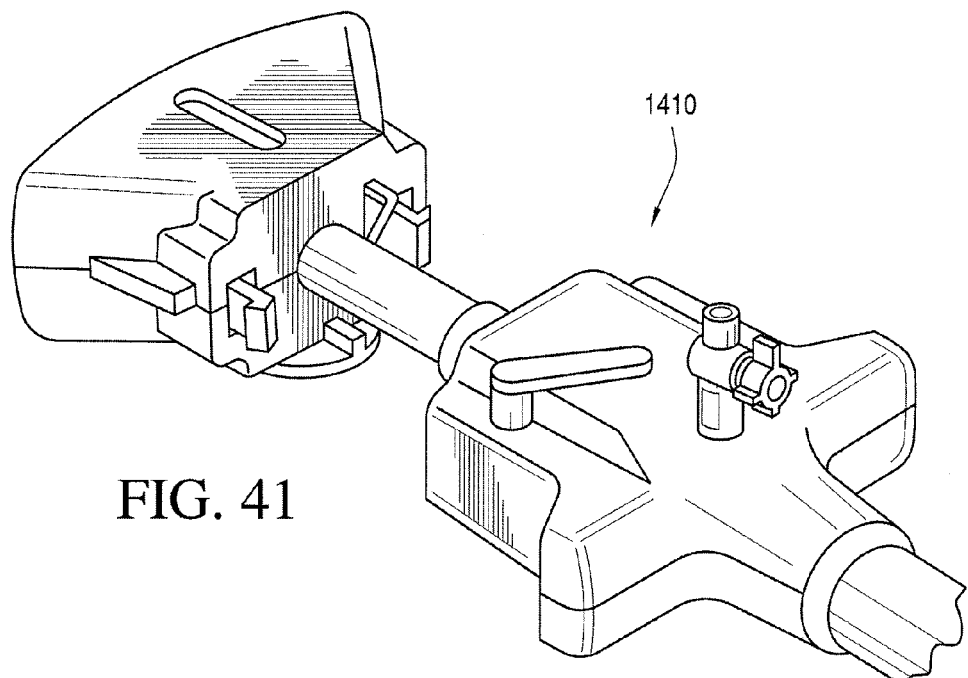
FIGS. 41 and 42 are perspective views showing another identification mechanism for utilization in accordance with the present invention.
Figure 42:
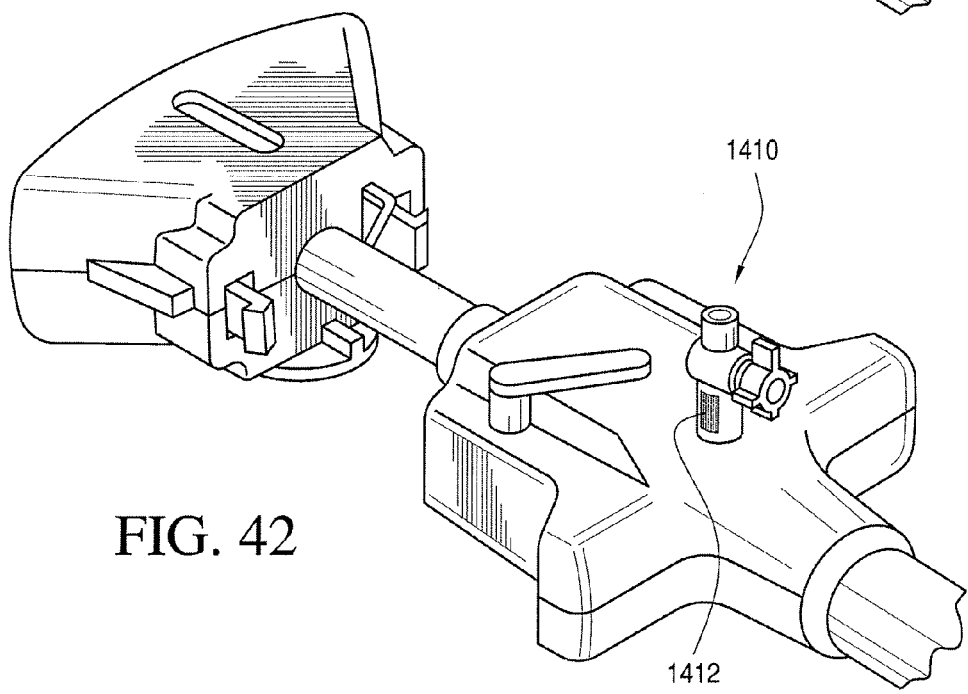

For example, when this technique is applied to trocars as disclosed with reference to FIGS. 41 and 42, the indicator material 1412 is applied to the stopcock region of the trocar 1410. With a semi-transparent material such as polycarbonate it would be possible to view the color of a strip of such material placed on the inside of the stopcock. After laparoscopic surgeries using carbon dioxide as the insufflation gas, the indicator material 1412 would change colors (see FIG. 42). The same material/concept could be adapted to detect fluids due to changes in pH levels also indicating use.

Thermochromic ink now currently available in the marketplace may be utilized for medical instrument labeling in accordance with the present invention. The Thermochromic ink described herein appears transparent, or a specific color, when applied, but when exposed to a heat above a specific temperature for a minimum specific time the ink becomes very apparent, or changes in color in apparent manner. As shown below the word REUSED on the labeling does not appear until the handle has gone through decontamination, hot washing or re-sterilization process thereby informing the user that the medical instrument is being reused. Also if the medical instrument fails during its reuse when it is sent to the original manufacturer for inspection, the manufacturer can document that it was during reuse that the failure occurred.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A medical instrument, comprising:
   a medical instrument body,
   a label including an indicator of exposure to fluids or solvents applied to the medical instrument body;
   wherein the indicator is a film printed with inks providing an indication of reuse or reprocessing of the medical instrument, and the film is a clear film and includes a first surface that is exposed for viewing when the label is applied to the medical instrument body and a second surface that faces the medical instrument body, and ink providing an indication of reuse or reprocessing of the medical instrument is printed upon the second surface which is not visible until contact with a fluid.

2. The medical instrument according to claim 1, wherein means are provided in the label for exposing the ink on the second surface to the fluid when the medical instrument is in contact with the fluid.

3. The medical instrument according to claim 1, wherein the label is further provided with an adhesive layer applied to the second surface and is directly secured to the medical instrument.

4. The medical instrument according to claim 3, wherein channels are formed in bonding points between the film and the medical instrument such that solutions can flow under the film from the edges thereof through the unbonded channels, and into contact with the ink.

5. The medical instrument according to claim 1, further including an adhesive backed substrate laminated to the second surface of the film, the adhesive backed substrate being directly secured to the medical instrument.

6. The medical instrument according to claim 5, wherein channels are formed in bonding points between the film and the adhesive backed substrate such that solutions can flow under the film from edges thereof through the unbonded channels, and into contact with the ink.

7. The medical instrument according to claim 5, wherein the film is applied to the adhesive backed substrate with a heat seal pattern around a perimeter of the top clear film.

8. The medical instrument according to claim 1, wherein perforations or holes are cut into the film providing a passageway for liquid to make its way to the second surface of the film.

9. The medical instrument according to claim 1, wherein channels are formed in bonding points between the film and the medical instrument such that solutions can flow under the film from the edges thereof through the unbonded channels, and into contact with the ink.

10. A medical instrument, comprising:
    a medical instrument body,
    a label including an indicator of exposure to fluids or solvents applied to the medical instrument body;
    wherein the label includes an opaque top film, the top film includes a first surface which is exposed for viewing upon application to the medical instrument body and a second surface which faces the medical instrument body and hidden from view, and adhesive bonds the second surface to the medical instrument in a manner permitting release of the label upon exposure to fluid revealing markings applied to a surface of the medical instrument, wherein the top film includes perforations, holes or laterally oriented channels cut into the top film providing a passageway for liquid to make its way to the second surface of the top film permitting fluid to flow under the top film and be caught for a period under the top film along the second surface to allow enough time to interact with the adhesive and disrupt the bond between the medical instrument and the top film.

11. A medical instrument, comprising:

a medical instrument body, a label including an indicator of exposure to fluids or solvents applied to the medical instrument body; wherein the indicator is a clear film printed with inks including a first surface that is exposed for viewing when the label is applied to the medical instrument body and said inks are printed upon the second surface which is not visible until contact with fluid; wherein the label.

12. A medical instrument, comprising:

a medical instrument body, a label including an indicator of exposure to fluids or solvents applied to the medical instrument body;

wherein the label includes a top layer and a base layer, and the top layer detaches from the base layer upon exposure to fluid; and wherein the top layer and the base layer are optically interactive such that the top layer and the base layer independently do not convey any recognizable text or other image but when laid one onto the other in a specific orientation and position the top layer and base layer align to produce a recognizable message.

13. The medical instrument according to claim 12, wherein the top layer and the base layer are combined to reveal a desired message using Optical Key technologies.

* * * * *